United States Patent [19]

Davis, deceased et al.

[11] Plant 4,863

[45] Jul. 6, 1982

[54] PEACH TREE (N30-12E)

[75] Inventors: Luther D. Davis, deceased, late of Davis, Calif.; by Donald R. Brooks, executor, West Sacramento, Calif.

[73] Assignee: The Regents of the University of California, Berkeley, Calif.

[21] Appl. No.: 198,787

[22] Filed: Oct. 20, 1980

[51] Int. Cl.[3] ..... A01H 5/03

[52] U.S. Cl. ..... Plt./43

[58] Field of Search ..... Plt./43

*Primary Examiner*—Robert E. Bagwill

*Attorney, Agent, or Firm*—Roger B. Webster

[57] ABSTRACT

A peach tree which is medium size, medium vigorous, upright-spreading, hardy, foliated with medium size, lanceolate leaves having a crenate margin, medium length petiole, and globose glands, blooms prolificly from hardy, medium-small, conic-pointed flower buds free from the stem and moderately pubescent, the flowers being large, showy, and pink; and is a regular and very productive bearer of large, uniform, globose, symmetrical, clingstone fruit having tough, thick, tenacious-to-flesh, yellow skin having a red blush, and fine, moderately firm, non-melting, light orange-yellow flesh.

2 Drawing Figures

CLASSIFICATION OF THE VARIETY

The present variety of peach tree is embraced by Class 43, Plants, of the U.S. Patent Office Manual of Classification.

BACKGROUND OF THE VARIETY

1. Field of the Invention

The inventor, Luther D. Davis, in the conduct of an extensive plant breeding program, originated a substantial number of new and distinct varieties of fruit trees, and which included the herein-claimed variety of peach tree. Such plant breeding program was undertaken by inventor Luther D. Davis at the University of California, Davis, Yolo County, Calif., and particularly in the experimental orchard at such location.

2. Prior Varieties

Among existing varieties of peach trees known to inventor Luther D. Davis, particular reference is made to Gaume (unpatented) and Carolyn (an unpatented selection of the U.S. Department of Agriculture) hereinafter mentioned for the purpose of comparison.

ORIGIN OF THE VARIETY

The present variety of peach tree was originated by inventor Luther D. Davis in the aforesaid experimental orchard, as a cross between two unnamed peach seedlings, which bore the identifications GH 8-14 and D30-3E.

ASEXUAL REPRODUCTION OF THE VARIETY

Subsequent to its origination, the present variety of peach tree was asexually reproduced, on behalf of inventor Luther D. Davis, and by budding on peach seedling rootstock, by a commercial nursery. Such asexual reproductions, in maturity at certain test plots, ran true to the original tree of the variety in all respects.

SUMMARY OF THE VARIETY

The present variety of peach tree is medium size, medium vigorous, upright-spreading, hardy, foliated with medium size, lanceolate leaves having a crenate margin, medium length petiole, and globose glands, blooms prolificly from hardy, medium-small, conic-pointed flower buds free from the stem and moderately pubescent, the flowers being large, showy, and pink; and is a regular and very productive bearer of large, uniform, globose, symmetrical, clingstone fruit having tough, thick, tenacious-to-flesh, yellow skin having a red blush, and fine, moderately firm, non-melting, light orange-yellow flesh.

The present variety of peach tree is characterized by fruit which—while slightly resembling the Gaume—is distinctive, in comparison, by absence of blossom end breakdown, by a larger stone less likely to split, and by a higher flavor fresh and canned.

The present variety of peach tree is further characterized by fruit which—enhanced by its large size and high flavor—processes into a very attractive canned peach; the fruit being in harvest approximately three days ahead of the Carolyn.

BRIEF DESCRIPTION OF THE DRAWING

The drawing is an illustration, by photographic reproduction in color, of separate fruit of the variety; one fruit being half cut away and the stone removed to show the flesh and the pit cavity. The drawing also illustrates separate stones of the variety.

DESCRIPTION OF THE VARIETY

The botanical details of this new and distinct variety of peach tree—with color definitions (except those in common color terms) referenced to Ridgway, Color Standards and Color Nomenclature (1912 edition)—are as follows:

Tree:
- *Size.*—Medium.
- *Vigor.*—Medium.
- *Growth.*—Upright-spreading.
- *Hardiness.*—Hardy.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.

*Color.*—Current season's shoots: Light green (Biscay Green — Plate XVII); slightly red on exposed surfaces. Young branches: Light brown (Cinnamon Brown — Plate XV). Older branches: Darker brown (Prout's Brown — Plate XV).

*Lenticels.*—Number: Medium. Size: Large. Often elongate and at right angles on 2 year-old shoots.

Leaves:

*Size.*—Medium. Average length from vigorous shoots — 16.9 cm. Average length from average shoots — 15.4 cm. Average width from vigorous shoots — 4.6 cm. Average width from average shoots — 4.2 cm. Length/width ratio is 3.6 for both vigorous and average shoots.

*Form.*—Lanceolate.

*Apex.*—Acuminate to attenuate.

*Thickness.*—Blade thin, flat to moderately folded, and often twisted.

*Color.*—Top side — dark green (Cedar Green — Plate XI). Under side — light green (Hellebore Green — Plate XVII).

*Margin.*—Crenate. Straight to moderately wavy.

*Petiole.*—Medium length — average 1.1 cm. on vigorous growth.

*Glands.*—Globose. Average number — 2-4. Position — usually 2 on petiole and 0-2 on base of leaf blade. Small.

Flower buds:

*Size.*—Medium — small.

*Length.*—Short.

*Hardiness.*—Hardy.

*Shape.*—Conic — pointed. Free of stem.

*Pubescence.*—Moderately pubescent.

Flowers:

*Blooming period.*—Prolific and relatively early compared to other cling peach varieties.

*Size.*—Large. Diameter of fully open flowers — 40-42 mm. Petal length — 18-19 mm. Petal width — 16-17 mm.

*Color of petals.*—Pink (Rosolane Pink — Plate XXVI).

*Stamens.*—Average number — 30. Length — 10-15 mm.

*Anthers.*—Red dorsally.

*Calyx lobes.*—Length — 5-6 mm. Width — 4 mm.

*Nectaries.*—Orange.

*Type.*—Showy.

*Number.*—Normally 2 per node.

Fruit:

*Maturity when described.*—Canning ripe — Aug. 1, 1979; 50% standard California cling peach maturity disc, 50% Dixon disc. Average firmness — 9.8 pounds pressure test.

*Season of maturity.*—Three days ahead of Carolyn.

*Size.*—Uniform. Large. Average diameter axially — 71.6 mm. Average transversely in suture plane — 74.5 mm. Average cheek to cheek — 76.0 mm.

*Form.*—Uniform. Globose. Symmetrical.

*Suture.*—Inconspicuous line. Slightly deeper at base and apex. Slight depression beyond pistil point.

*Ventral surface.*—Rounded. Slightly lipped at apex.

*Base.*—Rounded.

*Cavity.*—Conical to slightly elliptical. Smooth except for crease on ventral side. Uniform. Depth — 15-16 mm. Width — 15-17 mm. Length — 25-30 mm.

*Apex.*—Rounded.

*Pistil point.*—Small. Recessed. Oblique.

Skin:

*Texture.*—Tough.

*Thickness.*—Thick.

*Tenacity.*—Tenacious to flesh.

*Tendency to split.*—None.

*Pubescence.*—Medium. Long.

*Color.*—Ground color — yellow (Mustard Yellow — Plate XVI). Blush color — red (Pompeian Red — Plate XIII).

Flesh:

*Color.*—Yellow (Light Orange-Yellow — Plate III).

*Amygdalin.*—Scant.

*Juice.*—Moderate.

*Texture.*—Fine. Moderately firm. Non-melting.

*Fibers.*—None.

*Ripens.*—Evenly.

*Flavor.*—Mild.

*Aroma.*—Mild.

*Eating quality.*—Good.

*Canning quality.*—Excellent.

Stone:

*Type.*—Cling.

*Size.*—Medium. Average length — 35 mm. Average breadth — 28 mm. Average thickness — 21 mm.

*Form.*—Slightly obovate.

*Base.*—Very slightly oblique. Shorter on ventral edge.

*Hilum.*—Large. Oval.

*Apex.*—Rounded, with very slight tip.

*Sides.*—Equal. Plump.

*Surface.*—Moderately pitted and grooved, with grooves occurring near base and along ventral edge.

*Pits.*—In central area of stone and extending into dorsal shoulder. Shape variable, round to angular.

*Ridges.*—Rough. Slightly eroded, and entire surface area flecked with many small, shallow pock marks giving a rough, uneven appearance.

*Ventral surface.*—Narrow, with wings occurring along length of suture although often heavily eroded near base.

*Dorsal edge.*—Full. Somewhat protruding. Moderately winged, with deep narrow groove extending from base to near apex. Dorsal suture area just below apex often moderately eroded, with the dorsal groove becoming shallow and discontinuous in such area.

*Color.— Light brown (Cinnamon Buff — Plate XXIX).*

*Tendency to split.*—None.

Use:

*Major use.*—Canning.

Keeping quality: Good.

Resistance to insects and diseases: Average.

The peach tree and its fruit herein described may vary in slight detail due to climatic and soil conditions under which the variety may be grown; the present description being of the variety as grown in the Central Valley of California.

It is claimed:

1. A new and distinct variety of peach tree, substantially as illustrated and described, which regularly and with high productivity bears large, uniform, globose, symmetrical, clingstone fruit having fine, moderately firm, non-melting flesh; the fruit, which ripens about three days ahead of the Carolyn, is slightly similar to the Gaume but is distinctive—in comparison—by absence of blossom end breakdown, by a larger stone less likely to split, and by a higher flavor both fresh and canned.

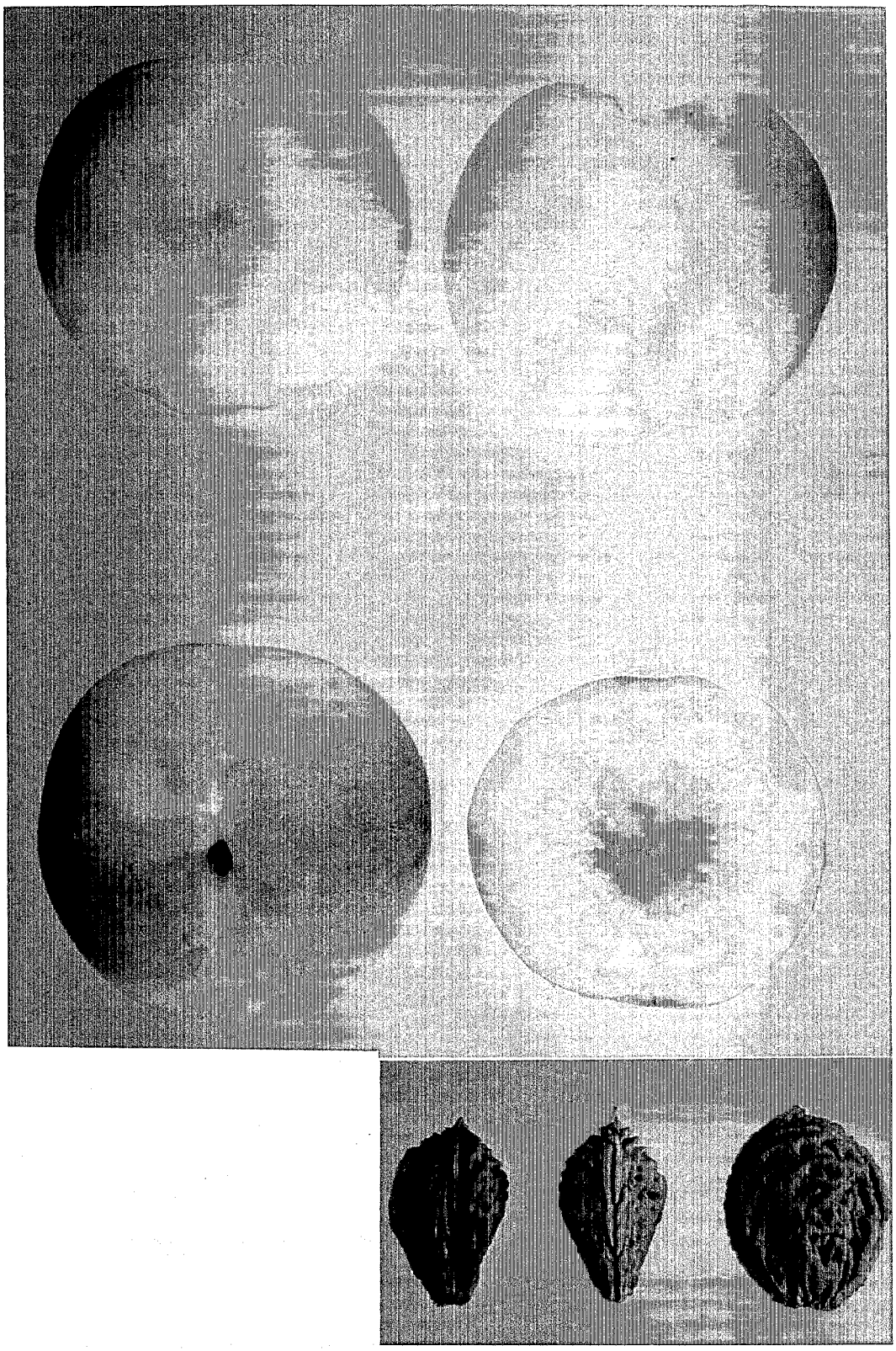

* * * * *